US007381402B2

(12) United States Patent
Lewis et al.

(10) Patent No.: US 7,381,402 B2
(45) Date of Patent: Jun. 3, 2008

(54) STABLE PHARMACEUTICAL SOLUTION FORMULATIONS FOR PRESSURIZED METERED DOSE INHALERS

(75) Inventors: David Lewis, Parma (IT); David Ganderton, Parma (IT); Brian Meakin, Parma (IT); Maurizio Delcanale, Parma (IT); Fausto Pivetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 11/065,569

(22) Filed: Feb. 25, 2005

(65) Prior Publication Data

US 2005/0220718 A1    Oct. 6, 2005

Related U.S. Application Data

(60) Provisional application No. 60/547,798, filed on Feb. 27, 2004.

(51) Int. Cl.
*A61K 9/12* (2006.01)
*A61K 9/08* (2006.01)
*A61K 31/47* (2006.01)
*A61K 31/4704* (2006.01)
*A61M 11/00* (2006.01)
*A61M 11/04* (2006.01)
*A61M 15/00* (2006.01)
*A61M 15/06* (2006.01)

(52) U.S. Cl. .................. 424/45; 424/43; 424/434; 514/253.08; 128/200.23; 128/203.12

(58) Field of Classification Search .................. 424/45
See application file for complete search history.

(56) References Cited

U.S. PATENT DOCUMENTS

| | | | |
|---|---|---|---|
| 3,361,306 A | 1/1968 | Grim | |
| 3,622,053 A | 11/1971 | Ryden | |
| 4,185,100 A | 1/1980 | Rovee et al. | |
| 4,499,108 A | 2/1985 | Sequeira et al. | |
| 4,579,854 A * | 4/1986 | Iwakuma et al. | ........... 514/312 |
| 4,584,320 A | 4/1986 | Rubin | |
| 4,835,145 A | 5/1989 | MacDonald | |
| RE33,024 E | 8/1989 | Iwakuma et al. | |
| 5,192,528 A | 3/1993 | Radhakrishnan et al. | |
| 5,415,853 A | 5/1995 | Hettche et al. | |
| 5,435,297 A | 7/1995 | Klein | |
| 5,605,674 A | 2/1997 | Purewal et al. | |
| 5,642,728 A | 7/1997 | Andersson et al. | |
| 5,653,961 A | 8/1997 | McNally et al. | |
| 5,676,930 A | 10/1997 | Jager | |
| 5,683,677 A | 11/1997 | Purewal et al. | |
| 5,695,743 A | 12/1997 | Purewal et al. | |
| 5,776,433 A | 7/1998 | Tzou et al. | |
| 5,891,419 A | 4/1999 | Cutie | |
| 5,954,047 A | 9/1999 | Armer et al. | |
| 5,955,058 A | 9/1999 | Jager et al. | |
| 6,004,537 A | 12/1999 | Blondino et al. | |
| 6,006,745 A | 12/1999 | Marecki | |
| 6,026,808 A | 2/2000 | Armer et al. | |
| 6,045,778 A * | 4/2000 | Jager et al. | .................. 424/45 |
| 6,045,784 A | 4/2000 | Ruebusch et al. | |
| 6,131,566 A | 10/2000 | Ashurst et al. | |
| 6,143,277 A | 11/2000 | Ashurst et al. | |
| 6,149,892 A | 11/2000 | Britto | |
| 6,150,418 A | 11/2000 | Hochrainer et al. | |
| 6,241,969 B1 | 6/2001 | Saidi et al. | |
| 6,253,762 B1 * | 7/2001 | Britto | .................. 128/200.14 |
| 6,290,930 B1 | 9/2001 | Blondino et al. | |
| 6,315,985 B1 | 11/2001 | Wu et al. | |
| 6,413,496 B1 | 7/2002 | Goodman et al. | |
| 6,451,285 B2 | 9/2002 | Blondino et al. | |
| 6,645,466 B1 | 11/2003 | Keller et al. | |
| 6,713,047 B1 | 3/2004 | Lewis et al. | |
| 6,716,414 B2 | 4/2004 | Lewis et al. | |
| 2001/0031244 A1 | 10/2001 | Lewis et al. | |
| 2003/0066525 A1 | 4/2003 | Lewis et al. | |
| 2003/0077230 A1 | 4/2003 | Blondino et al. | |
| 2003/0089369 A1 | 5/2003 | Lewis et al. | |

(Continued)

FOREIGN PATENT DOCUMENTS

EP    0 372 777    6/1990

(Continued)

OTHER PUBLICATIONS

U.S. Appl. No. 11/289,479, filed Nov. 30, 2005, Lewis et al.
U.S. Appl. No. 10/531,867, filed Sep. 16, 2005, Church et al.
U.S. Appl. No. 09/147,669, filed Feb. 24, 1999, Lewis et al.
U.S. Appl. No. 09/831,888, filed Jul. 19, 2001, Lewis et al.
U.S. Appl. No. 10/546,619, filed Aug. 23, 2005, Razzetti et al.
R.O. Williams III et al, "A study of an epoxy aerosol can lining exposed to hydrofluoroalkane propellants", *European Journal of Pharmaceutics and Biopharmaceutics*, vol. 44, pp. 195-203, (1997).
*ABPI Compendium of Data Sheets and Summaries of Product Characteristics*, Datapharm Publications Limited, London, pp. 81-82, (1996-97).
Paul A. Sanders, Ph.D., "Homogeneous Systems and Their Properties", *Handbook of Aerosol Technology*, Second Edition, Van Nostrand Reinhold Company, NY, p. 30, 1979.

(Continued)

*Primary Examiner*—Johann R. Richter
*Assistant Examiner*—James H Alstrum-Acevedo
(74) *Attorney, Agent, or Firm*—Oblon, Spivak, McClelland, Maier & Neustadt, P.C.

(57) ABSTRACT

Aerosol solution formulations for use in an aerosol inhaler which comprise 8-hydroxy-5-[(1R)-1-hydroxy-2-[[(1R)-2-(4-methoxyphenyl)-1-methylethyl]amino]-ethyl]-2(1H)-quinolinone or a salt thereof, in particular the hydrochloride salt (TA 2005), as an active ingredient, a propellant containing a hydrofluoroalkane, and a cosolvent, stabilized by addition of a specific small amount of a high concentrated phosphoric acid exhibit improved shelf life. The formulation may be optionally contained in a can having part or all of its internal metallic surfaces lined with an inert organic coating.

31 Claims, 1 Drawing Sheet

U.S. PATENT DOCUMENTS

| | | |
|---|---|---|
| 2003/0157028 A1 | 8/2003 | Lewis et al. |
| 2003/0190287 A1 | 10/2003 | Lewis et al. |
| 2003/0190289 A1 | 10/2003 | Lewis et al. |
| 2003/0206870 A1 | 11/2003 | Lewis et al. |
| 2004/0047809 A1 | 3/2004 | Lewis et al. |
| 2004/0062720 A1 | 4/2004 | Lewis et al. |
| 2004/0096399 A1 | 5/2004 | Lewis et al. |
| 2004/0184993 A1 | 9/2004 | Lewis et al. |
| 2005/0129621 A1 | 6/2005 | Davies et al. |
| 2005/0142071 A1 | 6/2005 | Lewis et al. |
| 2005/0152846 A1 | 7/2005 | Davies et al. |
| 2005/0220718 A1 | 10/2005 | Lewis et al. |
| 2006/0083693 A1 | 4/2006 | Lewis et al. |
| 2006/0120966 A1 | 6/2006 | Church et al. |

FOREIGN PATENT DOCUMENTS

| | | |
|---|---|---|
| EP | 0 504 112 | 9/1992 |
| EP | 0 504 112 A2 | 9/1992 |
| EP | 0 642 992 A2 | 3/1995 |
| EP | 0 653 204 | 5/1995 |
| EP | 0 911 048 | 4/1999 |
| EP | 1 157 689 | 11/2001 |
| GB | 1 525 181 | 9/1978 |
| GB | 2 326 334 | 12/1998 |
| WO | WO 91/11173 | 8/1991 |
| WO | WO 92/11236 | 7/1992 |
| WO | WO 92/20391 | 11/1992 |
| WO | WO 93/05765 | 4/1993 |
| WO | WO 93/11743 | 6/1993 |
| WO | WO 93/11747 | 6/1993 |
| WO | WO 93/18746 | 9/1993 |
| WO | WO 94/13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/18384 | 6/1996 |
| WO | WO 96/19198 | 6/1996 |
| WO | WO 96/19968 | 7/1996 |
| WO | WO 96/19969 | 7/1996 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | WO 98/56349 | 12/1998 |
| WO | WO 99/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | WO 00/30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |
| WO | WO 01/89480 | 11/2001 |
| WO | WO 03/074023 | 9/2003 |

OTHER PUBLICATIONS

G. Brambilla et al, "Modulation of Aerosol Clouds Produced by HFA Solution Inhalers", *Portable Inhalers*, pp. 155-159, (Nov. 26 & 27, 1998).

B. Meakin, "Fine Particle Dose Control of Solution Based pMDIs", *Drug Delivery to the Lungs IX*, The Aerosol Society, pp. 1-20, (Dec. 14 & 15, 1998).

S.S. Davis, "Physico-Chemical Studies on Aerosol Solutions For Drug Delievery I. Water-Propylene Glycol Systems", *International Journal of Pharmaceutics*, 1, 1978, pp. 71-83.

L. Harrison et al, "Twenty-eight-day Double-blind Safety Study of an HFA-134a Inhalation Aerosol System in Healthy Subjects", *J. Pharm. Pharmacol.*, 1996, vol. 48, pp. 596-600.

P. Hoet et al, "Epidemic of liver disease caused by hydrochlorofluorocarbons used as ozone-sparing substitutes of chlorofluorocarbons", *The Lancet*, 1997, vol. 350, pp. 556-559.

J. Daly, Jr., "Properties and toxicology of CFC alternatives", *Aerosol Age*, Feb. 1990, pp. 26-27, 40, 56 and 57.

D. Strobach, "Alternatives to CFCS" Part II, *Aerosol Age*, Jul. 1988, pp. 32-33, 42 and 43.

Tsi-Zong Tzou et al, "Drug Form Selection in Albuterol-Containing Metered-Dose Inhaler Formulations and Its Impact on Chemical and Physical Stability", *Journal of Pharmaceutical Sciences*, 1997, vol. 86, No. 12, pp. 1352-1357.

M.J. Kontny et al, "Issues Surrounding MDI Formulation Development with Non-CFC Propellants", *Journal of Aerosol Medicine*, 1991, vol. 4, No. 3, pp. 181-187.

I. P. Tansey, "Changing to CFC-Free Inhalers: The Technical and Clinical Challenges", *The Pharmacetical Journal*, 1997, vol. 259, pp. 896-898.

D. Tiwari et al, Compatibility Evaluation of Metered-Dose Inhaler Valve Elastomers with Tetrafluoroethane (P134a), a Non-CFC Propellant, *Drug Development and Industrial Pharmacy*, 1998, vol. 24, No. 4, pp. 345-352.

*Handbook of Pharmaceutical Excipients*, 3rd Ed., Kibbe Editor, pp. 7-9, 220-222, 234-235 and 560-561.

L. I. Harrison et al, "Pharmacokinetics and Dose Proportionality of Beclomethasone From Three Strengths of A CFC-Free Beclomethasone Dipropionate Metered-Dose Inhaler", *Biopharmaceutics & Drug Disposition*, 1997, vol. 18, No. 7, pp. 635-643.

Chet Leach, "Enhanced Drug Delivery Through Reformulating MDIs with HFA Propellants-Drug Deposition and Its Effect on Preclinical and Clinical Programs", *Respiratory Drug Delivery V*, 1996, pp. 133-144.

\* cited by examiner

STABLE PHARMACEUTICAL SOLUTION FORMULATIONS FOR PRESSURIZED METERED DOSE INHALERS

CROSS REFERENCES TO RELATED APPLICATIONS

This application claims priority to U.S. Provisional Application No. 60/547,798, filed on Feb. 27, 2004, and European Patent Application No. 04011424.1 filed on May 13, 2004, both of which are incorporated herein by reference in their entireties.

BACKGROUND OF THE INVENTION

1. Field of the Invention

The present invention relates to stable pharmaceutical solution formulations to be used with pressurized metered dose inhalers (MDIs) suitable for aerosol administration. In particular, the present invention relates to solutions to be used with pressurized metered dose inhalers (MDIs), which are suitable for aerosol administration, which contain a $\beta_2$-agonist, and which are stable at room temperature for a pharmaceutically acceptable shelf-life.

2. Discussion of the Background

Pressurized metered dose inhalers are well known devices for administering pharmaceutical products to the respiratory tract by inhalation.

Drugs commonly delivered by inhalation include bronchodilators such as $\beta_2$-agonists and anticholinergics, corticosteroids, anti-leukotrienes, anti-allergics, and other materials that may be efficiently administered by inhalation, thus increasing the therapeutic index and reducing side effects of the active material.

MDIs use a propellant to expel droplets containing the pharmaceutical product to the respiratory tract as an aerosol. Formulations for aerosol administration via MDIs can be solutions or suspensions. Solution formulations offer the advantage of being homogeneous with the active ingredient and excipients completely dissolved in the propellant vehicle or its mixture with suitable co-solvents such as ethanol. Solution formulations also obviate physical stability problems associated with suspension formulations so assuring more consistent uniform dosage administration.

For many years the preferred propellants used in aerosols for pharmaceutical use have been a group of chlorofluorocarbons which are commonly called Freons or CFCs, such as $CCl_3F$ (Freon 11 or CFC-11), $CCl_2F_2$ (Freon 12 or CFC-12), and $CClF_2$—$CClF_2$ (Freon 114 or CFC-114).

Recently, the chlorofluorocarbon (CFC) propellants such as Freon 11 and Freon 12 have been implicated in the destruction of the ozone layer and their production is being phased out.

Hydrofluoroalkanes ((HFAs) known also as hydro-fluoro-carbons (HFCs)) contain no chlorine and are considered less destructive to ozone and these are proposed as substitutes for CFCs.

HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems have been disclosed.

Due to the higher polarity of the HFA propellants, in particular of HFA 134a (dielectric constant $D \geq 9.5$), with respect to CFC vehicles ($D \leq 2.3$), HFA solution formulations may suffer to a greater extent from chemical stability problems with respect to the corresponding CFC formulations.

Preparation of stable HFA solution formulations is even more critical when bronchodilator $\beta_2$-agonists belonging to the class of the phenylalkylamino derivatives are concerned. Said drugs, like formoterol, 8-hydroxy-5-[(1R)-1-hydroxy-2-[[(1R)-2-(4-methoxyphenyl)-1-methylethyl]amino]ethyl]-2(1H)-quinolinone hydrochloride (hereinafter referred as TA 2005), salbutamol (albuterol) and others, may suffer from inherent chemical stability problems due to their susceptibility to oxidative conditions. Moreover, in view of the presence of some functional groups like formamide, a higher polarity of the vehicle may accelerate the rate of solvolysis reactions.

As for formoterol, the currently marketed CFC solution formulation (Foradil®) exhibits a limited shelf life, i.e., 12 months at refrigerator temperature, 4±2° C., and only 3 months at room temperature.

As for salbutamol, no formulation as an HFA solution for aerosol administration is currently on the market.

In the case of TA 2005, no formulation at all is currently available for aerosol administration.

In consideration of the problems outlined above, it would be highly advantageous to provide formulations in the form of HFA solutions to be administered by MDIs which afford pharmaceutical doses of $\beta_2$-agonists characterized by having an adequate shelf-life.

SUMMARY OF THE INVENTION

Accordingly, it is one object of the present invention to provide novel formulations in the form of HFA solutions to be administered by MDIs for providing pharmaceutical doses of a $\beta_2$-agonists into the lower respiratory tract of patients suffering from pulmonary diseases such as asthma and chronic obstructive pulmonary disease (COPD), characterized by having an adequate shelf-life.

It is another object of the present invention to provide novel formulations which comprise 8-hydroxy-5-[(1R)-1-hydroxy-2-[[(1R)-2-(4-methoxyphenyl)-1-methylethyl] amino]ethyl]-2(1H)-quinolinone or a salt thereof, in particular the hydrochloride salt (TA 2005).

It is an object of the present invention to provide formulations in the form of HFA solutions to be administered by MDIs for providing pharmaceutical doses of 8-hydroxy-5-[(1R)-1-hydroxy-2-[[(1R)-2-(4-methoxyphenyl)-1-methylethyl]amino]ethyl]-2(1H)-quinoline or a salt thereof, in particular the hydrochloride salt (TA 2005) with an acceptable shelf-life.

These and other objects, which will become apparent during the following detailed description, have been achieved by the inventors' discovery that aerosol formulations, which comprise 8-hydroxy-5-[(1R)-1-hydroxy-2-[[(1R)-2-(4-methoxyphenyl)-1-methylethyl]amino]ethyl-2 (1H)-quinolinone or a salt thereof, a liquefied HFA propellant, a co-solvent selected from pharmaceutically acceptable alcohols, and phosphoric acid, in which the formulation is in the form of a solution, and the phosphoric acid is present in an amount equivalent to 0.0004 to 0.040% by weight of 15 M phosphoric acid, based on the total weight of the formulation exhibit an improved shelf life.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
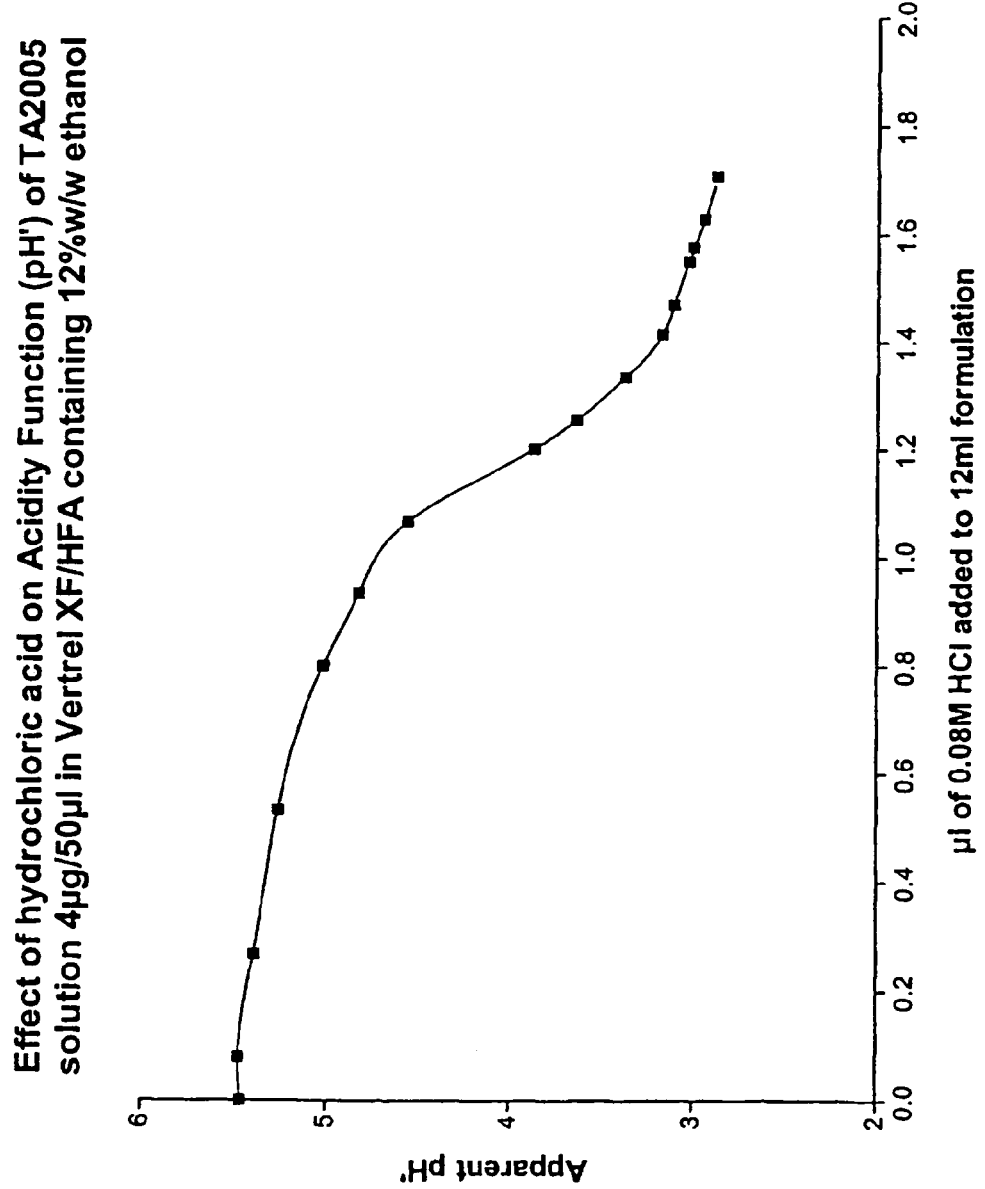
FIG. 1 shows the effect of hydrochloric acid on the acidity function (pH') of a TA 2005 solution (4 µg/50 µl) in VERTREL XF/HFA (HFA 43-10MEE) containing 20% w/w ethanol.

According to the present invention there is provided a pharmaceutical composition comprising a $\beta_2$-agonist belonging to the class of phenylalkylamino derivatives in a solution of a liquefied HFA propellant, a co-solvent selected from pharmaceutically acceptable alcohols, in which the apparent pH of the solution has been adjusted to between 2.5 and 5.0 by addition of small amounts of a mineral acid.

In particular it is provided a formulation comprising as active compound 8-hydroxy-5-[(1R)-1-hydroxy-2-[[(1R)-2-(4-methoxyphenyl)-1-methylethyl]amino]ethyl]-2(1H)-quinolinone or a salt thereof, in particular the hydrochloride salt, in a solution of a liquefied HFA propellant, a co-solvent selected from pharmaceutically acceptable alcohols, in which the apparent pH of the solution has been adjusted to between 2.5 and 5.0 by addition of a specific amount of high concentrated (i.e., more than about 10 M, preferably more than about 12 M and in particular about 15 M) phosphoric acid. The composition of the invention may be contained in a pressurized MDI having part or all of its internal metallic surfaces made of stainless steel, anodised aluminum or lined with an inert organic coating.

In fact, it has been found that, in the case of certain active ingredients such as $\beta_2$-agonists, their chemical stability in HFA solution formulations could be dramatically improved by a proper and combined selection of the kind of cans as well as the apparent pH range. The attribution 'apparent' is used as pH is indeed characteristic of aqueous liquids where water is the dominant component (Mole Fraction >0.95). In relatively aprotic solvents, such as the HFA-ethanol vehicles used in these studies, protons are non-hydrated; their activity coefficients differ significantly from those in aqueous solution. Although the Nernst equation with respect to EMF applies and the pH-meter glass electrode system will generate a variable milli-volt output according to proton concentration and vehicle polarity, the "pH" meter reading is not a true pH value. The meter reading represents an apparent pH or acidity function (pH').

When TA 2005 was titrated with a strong acid in a model vehicle system commercially available (HFA 43-10MEE, VERTREL XF, Dupont), according to a method developed by the applicant, the pH' profile exhibited a shallow negative slope to about pH'=5.0; thereafter the acidity function dropped abruptly.

On the other hand, the use of inert containers avoids the leaching of metal ions or alkali as a consequence of the action of the acid contained in the formulation on the inner walls of the cans. Metal ions such $Al^{3+}$ or alkali respectively deriving from the conventional aluminum or glass cans could in turn catalyze radical oxidative or other chemical reactions of the active ingredient which give rise to the formation of degradation products.

According to another embodiment of the present invention there is also provided a pharmaceutical composition further containing a low volatility component in such a way as to, besides increasing the mass median aerodynamic diameter (MMAD) of the aerosol particles on actuation of the inhaler as explained in the following, further improve the stability of the formulation. In fact, the addition of a low volatility component with a reduced polarity with respect to the co-solvent such as an ester may allow either a reduction in the amount of acid to be added for adjusting the pH and diminish the polarity of the medium so limiting the possible uptake of environmental water.

According to another embodiment of the invention, there is provided a pressurised MDI consisting of a coated container filled with a pharmaceutical composition consisting of a solution of TA 2005 in HFA 134a as a propellant in turn containing ethanol as a co-solvent with or without isopropyl myristate as a low volatility component, the apparent pH of said solution having been adjusted to between 3.0 and 5.0 by addition of small amounts of a mineral acid.

It has in particular been found that in presence of lower concentrations of TA 2005 and for example with a concentration of 1 µg/50 µl (0.002% w/v) in the presence of 0.08 M HCl, the pH interval is of 2.5-5.5 and the degree of stabilization is determined by the percent amount of the acid.

Further experiments have shown, and it will be described in detail in the following, that TA 2005 can be better stabilized with high concentrated phosphoric acid, and in particular with 85% (about 15 M) phosphoric acid.

In fact, it has now been found that TA 2005 chemical degradation in a solution of a HFA propellant and a co-solvent not only depends on the acidity function of the solution, but it is also catalyzed by trace levels of metal ions and that TA 2005 stability can be enhanced by adding to the solution specific amounts of high concentration phosphoric acid both to adjust the apparent pH in a well defined range and to sequester metal ions.

Moreover, it has been found that the stabilizing effect of phosphoric acid is not strictly correlated with its w/w percent amount in the formulation and it is present in a concentration interval from 0.0004 to 0.040% by weight, based on the total weight of the formulation.

The corresponding apparent pH interval is of 2.5 to 5.5, preferably 3.0 to 5.5, more preferably 3.5 to 5.0.

However, a person sufficiently skilled in the art can easily apply the teachings of the present invention to the preparation of HFA solution formulations containing other active ingredients bearing functional groups sensitive to hydrolytic and/or oxidative reactions, such as formamide and cathecol respectively.

WO 97/47286, EP 513127, EP 504112, WO 93/11747, WO 94/21228, WO 94/21229, WO 96/18384, WO 96/19198, WO 96/19968, WO 98/05302, WO 98/34595, and WO 00/07567 disclose HFA formulations in the form of suspensions in which $\beta_2$-agonists such formoterol and salbutamol are either exemplified and/or claimed.

WO 99/65464 discloses HFA formulations containing two or more active ingredients in which at least one is in suspension. The preferred formulations comprise salbutamol sulfate in suspension.

WO 98/34596 discloses solution compositions for use in an aerosol inhaler, comprising an active material, a propellant containing a hydrofluoroalkane (HFA), a cosolvent and further comprising a low volatility component to increase the mass median aerodynamic diameter (MMAD) of the aerosol particles on actuation of the inhaler. Said application does not address the technical problem of the chemical stability of the active ingredient but it rather concerns the drug delivery to lungs.

WO 00/30608 discloses pressurized MDIs for dispensing a solution of an active ingredient in a hydrofluorocarbon propellant, a co-solvent and optionally a low-volatility component characterized in that part or all of the internal surfaces of said inhalers consist of stainless steel, anodised aluminum or are lined with an inert organic coating. The examples are of only steroids and anticholinergic agents. However, the use of coated containers, even in the presence of an organic acid, is not sufficient for providing stable solution formulations of a phenylalkylamino derivative such as salbutamol.

EP 673240 discloses the use of acids as stabilizers for preventing the chemical degradation of the active ingredient in aerosol solution formulations comprising HFAs. Most examples relate to ipratropium bromide, an anticholinergic drug and only one example is presented for a $\beta_2$-agonist, i.e., fenoterol. Although salbutamol is claimed, no exemplary formulations are provided. Moreover, the stability data are reported only for ipratropium and no distinction is made between the use of organic and inorganic acids. However, salbutamol cannot be stabilized at all by addition of organic acids even when stored in coated cans. Furthermore, apart from ipratropium bromide, in EP 673240 no guidance is given with respect to the amount of acid which has to be added in order to stabilize the medicaments without compromising the stability of the whole composition in the can. The only hint can be found on page 5, lines 15 to 16, which says that an amount of inorganic acid should be added to obtain a pH value from 1 to 7, a very broad and generic range.

WO 98/34596 discloses solution formulations containing a propellant and a physiologically acceptable polymer which could help the solubilization and the stability as well of the active ingredients.

WO 00/06121 discloses propellant mixtures for aerosol dinitrogen monoxide and a hydrofluoroalkane in the preparation of suspension and solution aerosols. The use of dinitrogen monoxide may improve the stability on storage of oxidation-sensitive active ingredients. As for $\beta_2$-agonists such as levosalbutamol sulfate, formoterol fumarate, and salmeterol xinafoate, only examples of suspensions are reported.

WO 99/65460 discloses pressurized MDIs containing stable formulations of a $\beta_2$-agonist drug in suspension or solution. The examples refer to solutions of formoterol fumarate containing an HFA propellant and ethanol as co-solvent, filled in conventional aluminum or plastic coated glass cans. Samples stored under accelerated conditions (40° C., 75% relative humidity) for a very short period, one month, exhibited about 10% loss of drug. According to pharmaceutical guidelines on stability, loss of 10% of active ingredient does not meet the criteria of acceptance. Moreover, as it is evident from the data reported in Example 2 of the present application, by following the teaching of WO 99/65460, stable formoterol solution formulations cannot be provided. The applicant has indeed demonstrated that the presence of low-volatility components does not substantially affect the chemical stability of the compositions. In some cases, they could even improve it.

In EP 1 157 689 ('689) (WO 01/89480), stability data of a HFA 134a solution formulation containing 8-hydroxy-5-[(1R)-1-hydroxy-2-[[(1R)-2-(4-methoxyphenyl)-1-methylethyl]amino]ethyl]-2(1H)-quinolinone hydrochloride (TA 2005) 3.5 µg/50 µl dose, 12% w/w ethanol, 1% w/w isopropyl myristate stabilised by different amounts of HCl 0.08M (1.0 and 1.4 µl) were reported (Example 7). The formulations were reported to be provided with quite good stability if stored in upright position and if present in relatively high concentrations (3.5 µg/50 µl) (Comparative Example 1). Nevertheless, when the present inventors repeated the test with a rather low concentration (Example 2), they noticed a progressive degradation of the active ingredient in the formulation. Moreover, the formulation exemplified contained isopropyl myristate as a low volatility compound in order to increase the MMAD (mass median aerodynamic diameter) of the delivered particles. It has been subsequently found that it would be highly advantageous to provide highly efficient TA 2005 formulations characterised by a deeper lung penetration by virtue of a significant fraction, of at least 30%, of fine particles, with a diameter equal or less than 1.1 µm. Therefore the low volatility compound is preferably avoided.

It has been subsequently also found that in this kind of highly efficient formulations, characterized by the presence of a fraction of particles equal to or less than 1.1 µm higher than 30% and even than 50% or more, TA 2005 can be present in a very low concentration, starting from 0.0005% w/v based on the total volume of the composition.

Such compositions have been described in another previous application of the applicant, WO 03/074025, wherein stability data of a HFA solution formulation comprising 8-hydroxy-5-[(1R)-1-hydroxy-2-[[(1R)-2-(4-methoxyphenyl)-1-methylethyl]amino]ethyl]-2(1H)-quinolinone hydrochloride (TA 2005) stabilized by HCl were reported. The stability was determined on a formulation delivering 4 µg of active compound per actuation, stored upright at 5° C.: in said refrigerated conditions, after nine months, the TA 2005 assay was higher than 95%. However, it has then been found by the present inventors that when present in lower concentrations and in other storage conditions, the active ingredient in the formulation rapidly degrades. Moreover, the other hand, refrigeration is undesirable because many patients are required to carry the aerosol canisters on their persons.

According to the first aspect of the present invention, it has been found by the present inventors that, while according to the previous disclosure of WO 03/074025 the preferred mineral acid was hydrochloric acid, the chemical stability of 8-hydroxy-5-[(1R)-1-hydroxy-2-[[(1R)-2-(4-methoxyphenyl)-1-methylethyl]amino]ethyl]-2(1H)-quinoline and its salts is enhanced by small amounts of high concentrated phosphoric acid, more than 10M, preferably about 15M phosphoric acid, preferably comprised between 0.0008% and 0.01% w/w in the formulation, wherein the expression "% w/w" means the weight percentage of the component with respect to the total weight of the composition. The mineral acid that better stabilizes the active ingredient 8-hydroxy-5-[(1R)-1-hydroxy-2-[[(1R)-2-(4-methoxyphenyl)-1-methylethyl]amino]ethyl]-2(1H)-quinoline and its salts in the formulation is phosphoric acid, in particular highly concentrated phosphoric acid.

The aerosol formulations containing phosphoric acid are surprisingly stable at room temperature for a long life time.

According to a further aspect of the present invention there is provided a method of filling an aerosol inhaler with a composition of the invention, the method comprising:

(a) preparing a solution of one or more active ingredients in one or more co-solvents optionally containing an appropriate amount of a low volatility component;

(b) filling the device with said solution;

(c) adding a pre-determined amount of a strong mineral acid;

(d) adding a propellant containing a hydrofluoroalkane (HFA); and (e) crimping with valves and gassing.

Active ingredients which may be used in the aerosol compositions of the present invention are short- and long-acting $\beta_2$-adrenergic agonists such as salbutamol, formoterol, salmeterol, TA 2005 and salts thereof and their combinations with steroids such as beclomethasone dipropionate, fluticasone propionate, budesonide and its 22R-epimer or with anticholinergic atropine-like derivatives such as ipratropium bromide, oxitropium bromide, tiotropium bromide.

Preferably the active ingredient is a long acting $\beta_2$-agonist belonging to the formula sketched below

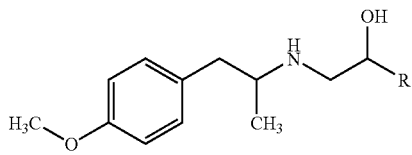

wherein R is more preferably 8-hydroxy-2(1H)-quinolinon-5-yl, its salts or one of its corresponding stereoisomers. The preferred salt is the hydrochloride salt, also referred to as TA 2005. Although the preferred formulations of the invention are in the form of solutions, in case of the combinations, one of the two active ingredients could be present in suspension.

TA 2005 may be prepared as described in U.S. Pat. No. RE 33,024, which is incorporated herein by reference.

It is preferred that the formulation be suitable for delivering a therapeutic amount of the active ingredient in one or two actuations. Preferably the formulation will be suitable for delivering 0.5-6 μg/dose, more preferably 1-4 μg/dose, and in particular 1 to 2 μg/dose or 2 to 3 μg/dose. By "dose" it is meant the amount of active ingredient delivered by a single actuation of the inhaler.

The formulations of the present invention are preferably contained in cans having part or all of the internal surfaces made of anodised aluminum, stainless steel or lined with an inert organic coating. Examples of preferred coatings are epoxy-phenol resins, perfluoroalkoxyalkane, perfluoroalkoxyalkylene, perfluoroalkylenes such as polytetrafluoroethylene, fluorinated-ethylene-propylene, polyether sulfone and copolymers of fluorinated-ethylene-propylene polyether sulfone. Other suitable coatings could be polyamide, polyimide, polyamideimide, polyphenylene sulfide or their combinations.

To further improve the stability, cans having a rolled-in rim and preferably a part or full rollover rim are used.

The formulation is actuated by a metering valve capable of delivering a volume of between 50 μl and 100 μl.

Metering valves fitted with gaskets made of chloroprene-based rubbers can preferably be used to reduce the ingress of moisture which, as previously mentioned, can adversely affect the stability of the drug during storage. Optionally, further protection can be achieved by packaging the product in a sealed aluminum pouch.

The hydrofluorocarbon propellant is preferably selected from the group of HFA 134a, HFA 227 and mixtures thereof.

The co-solvent is usually an alcohol, preferably ethanol.

The low volatility component, when present, has a vapor pressure, at 25° C., lower than 0.1 kPa, preferably lower than 0.05 kPa. Advantageously, it could be selected from the group of glycols, particularly propylene glycol, polyethylene glycol and glycerol or esters, for example ascorbyl palmitate, isopropyl myristate and tocopherol esters.

The compositions of the present invention may contain from 0.1 to 10% w/w of said low volatility component, preferably between 0.3 to 5% w/w, more preferably between 0.4 and 2.0% w/w.

Propylene glycol, polyethylene glycol, glycerol with residual water less than 0.1% w/w and esters of long-chain fatty acids are the preferred low-volatility components. More preferred are those with a dipole moment less than 2.0 or with a dielectric static constant less than 20, preferably less than 10. Particularly preferred is isopropyl myristate.

The function of the low volatility component is to modulate the MMAD of the aerosol particles and optionally to further improve the stability of the formulation. With respect to the latter aspect, particularly preferred is the use of isopropyl myristate.

The apparent pH range is advantageously comprised between 2.5 and 5.5, preferably between 3.0 and 5.5, even more preferably between 3.5 and 5.0.

Rather concentrated, i.e., more than about 10 M, preferably more than about 12 M, and most preferably about 15 M phosphoric acid is used to adjust the apparent pH. In the examples that follow 85%, i.e., 15.2M phosphoric acid has been used. The amount of acid to be added to reach the desired apparent pH will be pre-determined in the model vehicle reported before In a particularly preferred embodiment, the active ingredient is 8-hydroxy-5-[(1R)-1-hydroxy-2-[[(1R)-2-(4-methoxyphenyl)-1-methylethyl]amino]ethyl]-2(1H)-quinolinone or its salt is stabilized with rather concentrated, preferably about 15 M phosphoric acid. In particular, it is preferred to add phosphoric acid in an amount equivalent to 0.0004 to 0.040% w/w of 15M phosphoric acid, based on the total weight of the composition, preferably 0.0008 to 0.020% w/w of 15M phosphoric acid, based on the total weight of the composition, more preferably 0.001 to 0.010% w/w of 15M phosphoric acid, based on the total weight of the composition, still more preferably 0.002 to 0.0075% w/w of 15 M phosphoric acid, based on the total weight of the composition. For the purposes of the present invention a still higher concentrated phosphoric acid other than 15 M can be utilized. In this case, the person skilled in the art will be able to determine the right percent amount in view of the disclosure in the present application. In this embodiment, it may also be preferred to avoid addition of the low-volatility component to increase the fraction of particles with a diameter less than or equal to 1.1 μm to at least 30% and to provide deeper lung penetration.

In the case of the hydrochloride salts or TA 2005, the concentration will vary between 0.0005% and 0.024% w/v, based on the total volume of the composition, in order to deliver 0.5-6 μg per actuation, preferably between 0.001% and 0.016% w/v, based on the total volume of the composition, in order to deliver 1 to 4 μg per actuation, more preferably between 0.001% and 0.008% w/v, based on the total volume of the composition, in order to deliver 1 to 2 μg per actuation. For instance, for 1 and 2 μg/dose, wherein a 63 μl metering volume is used, the final concentrations of TA 2005 hydrochloride delivered per actuation would be 0.0016% and 0.0032% w/v, respectively, based on the total volume of the composition. The amount of co-solvent in the composition is suitably 5 to 30% w/w, preferably 5 to 25% w/w, more preferably 5 to 20% w/w, based on the total weight of the composition.

In these conditions, the stability of TA 2005 is enhanced also at the very low dose strength of 1 μg per actuation.

The apparent pH value is preferably comprised between 3.5 and 5.0.

In the examples that follow, the stabilizing effects of phosphoric acid were also tested in a TA 2005 HFA formulation comprising as a further active ingredient budesonide, an anti-inflammatory 20-ketosteroid which meets with chemical stability problems when formulated in a HFA aerosol solution formulation.

Other features of the invention will become apparent in the course of the following descriptions of exemplary embodiments which are given for illustration of the invention and are not intended to be limiting thereof.

EXAMPLES

In the following examples, and throughout this specification, all parts and percentages are by weight, and all temperatures are in degrees Celsius, unless expressly stated to be otherwise.

Example 1

Effect of Hydrochloric Acid on Solution pH' (Acidity Function)

1.0 M hydrochloric acid was added incrementally to 50 ml of HFA 43-10MEE (VERTREL XF) containing 20% w/w ethanol and the pH' was measured after each aliquot of acid. FIG. 1 shows the resultant titration curve normalized to the usual fill volume of a pMDI can (12ml). The pH' profile exhibits a shallow negative slope to about pH'=5.0; thereafter the acidity function drops abruptly.

Comparative Example 1 (corresponding to Example 7 of EP 1 157 689). Stability of acidified TA 2005-HFA 134a solutions in cans coated with a fluorocarbon polymer.

A solution of TA 2005 (3.5 µg/50 µl) was prepared by dissolving 0.84 mg of the active ingredient in HFA 134a containing 12% w/w ethanol and 1.0% w/w of isopropyl myristate. pMDI coated cans containing 1.0, 1.4, and 1.8 µl of 0.08 M hydrochloric acid (corresponding respectively to an apparent pH of about 4.8, 3.2, and 2.9) were set down on storage, upright at 50° C., and samples taken for analysis of TA 2005 contents at appropriate intervals.

The stability data obtained are given in Table 1.

Each value is expressed as percent nominal drug concentration.

The results indicate that the formulations containing from 1.0 to 1.4 µl of 0.08 M HCl, whose apparent pH is comprised between 3.0 and 5.0 are stable for almost three months at 50° C.

TABLE 1

TA 2005 formulations - Stability data at 50° C.

| 0.08M HCl µl per can | Initial | Storage Condition 50° C.; 22 days upright | 50° C.; 83 days upright |
|---|---|---|---|
| 1.0 | 100.0 | 98.3 | 99.4 |
| 1.4 | 100.0 | 98.2 | 98.8 |
| 1.8 | 100.0 | 90.2 | 88.1 |

Example 2

Two aluminum canisters having the internal surface coated with teflon and fitted with commercial valves having a 63 µl metering chamber were filled with the following formulations shown in Table 2.

TABLE 2

| Components | Amounts per unit | | | |
|---|---|---|---|---|
| | mg | % | mg | % |
| TA 2005 (1 µg/63 µl) | 0.154 | 0.0016 w/v | 0.154 | 0.0016 w/v |
| Ethanol | 1650.0 | 15 w/w | 1650.0 | 15 w/w |
| Hydrochloric acid 0.1M | 2.00* | 0.018 w/w | 3.00 | 0.027 w/w |
| HFA 134a q.s. to 9.45 ml | 9347.85 | — | 93467.85 | — |

*equivalent to 2.0 µl

A stability study was carried out by storing the formulations in upright cans at 40° C. and 75% relative humidity. After three months of storage under these conditions the percent amount of TA 2005 was 73% and 77% respectively.

According to the results of Comparative Example 1 and Example 2, TA 2005 (8-hydroxy-5-[(1R)-1-hydroxy-2-[[(1R)-2-(4-methoxyphenyl)-1-methylethyl]amino]ethyl]-2(1H)-quinolinone hydrochloride) can be stabilized by the use of hydrochloric acid if TA 2005 is present in the solution formulation in a comparatively high concentration (3.5 µg/50 µl). However, if it is present in a rather low concentration as desired for this kind of active ingredient (e.g. 1 µg or 2 µg /63 µl), it can no longer be stabilized by the use of hydrochloric acid. The active ingredient 8-hydroxy-5-[(1R)-1-hydroxy-2-[[(1R)-2-(4-methoxyphenyl)-1-methylethyl]amino]ethyl]-2(1H)-quinolinone hydrochloride is a very potent long acting β$_2$-agonist active at a very low dosage-strength, which should be applied in a low concentration. Moreover, the storage in a refrigerator should be avoided.

As it will be demonstrated by the results of the following example, 8-hydroxy-5-[(1R)-1-hydroxy-2-[[(1R)-2-(4-methoxyphenyl)-1-methylethyl]amino]ethyl]-2(1H)-quinoline hydrochloride can, however, be stabilized also in very low concentrations (e.g. 1 µg/63 µl) by the use of phosphoric acid in an amount equivalent to 0.0004 to 0.040% w/W, preferably 0.0008 to 0.020% w/w, more preferably 0.001 to 0.010% w/w, still more preferably 0.002 to 0.0075% w/w of 15 M phosphoric acid, based on the total weight of the composition.

Example 3

An analogous formulation (see, Table 3) for delivering a nominal dose of 1 µg of active ingredient per actuation was prepared with the composition as follows, utilizing phosphoric acid as a stabilizer in place of hydrochloric acid.

TABLE 3

| Components | Amounts per unit | |
|---|---|---|
| | mg | % |
| TA 2005 (1 µg/63 µl) | 0.154 | 0.0016 w/v (0.0014 w/w) |
| Ethanol | 1650.0 | 15.00 w/w |
| Phosphoric acid 15.2M | 0.05 to 0.6 | 0.00045 to 0.0054 w/w |
| HFA 134a q.s. to 9.72 ml | q.s. to 11,000 | — |

Analogously, formulations capable of delivering a nominal dose of 0.5, 1.5, 2, 2.5, 3, 3.5, or 4 µg of active ingredient per actuation may also be prepared.

The formulation of Table 3 (120 actuations canister, overage of 30 actuations) was filled in aluminum canisters having the internal surface coated with teflon and fitted with commercial valves having a 63 µl metering chamber.

A stability study was carried out by storing the formulation in upright and inverted cans at 40° C. and 75% relative humidity. After three months of storage under these conditions the percent amount of TA 2005 was very good with residual percent amount of TA 2005 up to 98% in the range of phosphoric acid of 0.001 to 0.0027% w/w.

Example 4

The two compositions containing TA 2005 and budesonide as active ingredients and two different concentrations of phosphoric acid as shown in Table 4 were prepared.

TABLE 4

| Component | Amounts per unit | | | |
|---|---|---|---|---|
|  | mg | % w/w | mg | % w/w |
| Budesonide | 30.8 | 0.2800 | 30.8 | 0.2800 |
| TA 2005 (CHF 4226) | 0.154 | 0.0014 | 0.154 | 0.0014 |
| Absolute Ethanol | 1650 | 15.0000 | 1650 | 15.0000 |
| Water | 16.5 | 0.1500 | 16.5 | 0.1500 |
| Phosphoric acid 85% (15.2 M) | 0.35 | 0.0032 | 0.7 | 0.0064 |
| HFA 134a | 9302.196 | 84.5654 | 9301.846 | 84.5622 |
| Total | 11000 | 100.0000 | 11000 | 100.0000 |

Volume of the valve: 63 µl; strength: TA 2005 1 µg+budesonide 200 µg/actuation; no. of actuations: 120 (34 overfilling doses).

The two active ingredients in the compositions were stable after three months storage at 40° C. and 75% relative humidity, giving residual percent amounts of at least 95% TA 2005 and about 100% of budesonide.

Therefore phosphoric acid is efficacious to stabilize TA 2005 also in the combination and in presence of small quantities of water.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An aerosol formulation, which comprises 8-hydroxy-5-[(1R)-1-hydroxy-2-[[(1R)-2-(4-methoxyphenyl)-1-methylethyl]amino]ethyl-2(1H)-quinolinone or a salt thereof, a liquefied HFA propellant, a co-solvent selected from pharmaceutically acceptable alcohols, and phosphoric acid, wherein said formulation is in the form of a solution, and said phosphoric acid is present in an amount equivalent to 0.0004 to 0.040% by weight of 15 M phosphoric acid, based on the total weight of the formulation, and
wherein said 8-hydroxy-5-[(1R)-1-hydroxy-2-[[(1R)-2-(4-methoxyphenyl)-1-methylethyl]amino]ethyl]-2(1H)-quinolinone or salt thereof is present in an amount of 0.0005% to 0.0032% w/v, based on the total volume of the formulation.

2. The formulation according to claim 1, wherein said liquefied HFA propellant is at least one member selected from the group consisting of HFA 134a, HFA 227, and mixtures thereof.

3. The formulation according to claim 1, wherein said co-solvent is ethanol.

4. The formulation according to claim 1, wherein said phosphoric acid is present in an amount equivalent to 0.0008 to 0.020% by weight of 15M phosphoric acid, based on the total weight of the formulation.

5. The formulation according to claim 1, wherein said phosphoric acid is present in an amount equivalent to 0.001 to 0.010% by weight of 15M phosphoric acid, based on the total weight of the formulation.

6. The formulation according to claim 1, which has an apparent pH of between 2.5 and 5.5.

7. The formulation according to claim 1, which has an apparent pH of 3.0 to 5.5.

8. The formulation according to claim 1, which has an apparent pH of 3.5 to 5.0.

9. The formulation according to claim 1, wherein said 8-hydroxy-5-[(1R)-1-hydroxy-2-[[(1R)-2-(4-methoxyphenyl)-1-methylethyl]amino]ethyl]-2(1H)-quinolinone or salt thereof is present in an amount of 0.0005% to 0.0016% w/v, based on the total volume of the formulation.

10. The formulation according to claim 1, wherein said co-solvent is present in an amount of 6% to 30% by weight, based on the total weight of the formulation.

11. The formulation according to claim 1, wherein said co-solvent is present in an amount of 6% to 25% by weight, based on the total weight of the formulation.

12. A pressurized metered dose inhaler, which contains a formulation, wherein said formulation comprises 8-hydroxy-5-[(1R)-1-hydroxy-2-[[(1R)-2-(4-methoxyphenyl)-1-methylethyl]amino]ethyl]-2(1H)-quinolinone or a salt thereof, a liquefied HFA propellant, a co-solvent selected from pharmaceutically acceptable alcohols, and phosphoric acid, wherein said formulation is in the form of a solution, and said phosphoric acid is present in an amount equivalent to 0.0004 to 0.040% by weight of 15 M phosphoric acid, based on the total weight of the formulation, and
wherein said 8-hydroxy-5-[(1R)-1-hydroxy-2-(4-methoxyphenyl)-1-methylethyl]amino]ethyl]-2(1H)-quinolinone or salt thereof is present in said formulation in an amount of 0.0005% to 0.0032% w/v, based on the total volume of the formulation.

13. The pressurized metered dose inhaler according to claim 12, wherein said liquefied HFA propellant is at least one member selected from the group consisting of HFA 134a, HFA 227, and mixtures thereof.

14. The pressurized metered dose inhaler according to claim 12, wherein said co-solvent is ethanol.

15. The pressurized metered dose inhaler according to claim 12, wherein said phosphoric acid is present in said formulation in an amount equivalent to 0.0008 to 0.020% w/w of 15 M phosphoric acid, based on the total weight of the formulation.

16. The pressurized metered dose inhaler according to claim 12, wherein said phosphoric acid is present in said formulation in an amount equivalent to 0.00 1 to 0.010% by weight of 15M phosphoric acid, based on the total weight of the formulation.

17. The pressurized metered dose inhaler according to claim 12, wherein said solution has an apparent pH of between 2.5 and 5.5.

18. The pressurized metered dose inhaler according to claim 12, wherein said formulation has an apparent pH of 3.0 to 5.5.

19. The pressurized metered dose inhaler according to claim 12, wherein said formulation has an apparent pH of 3.0 to 5.0.

20. The pressurized metered dose inhaler according to claim 12, wherein said 8-hydroxy-5-[(1R)-1-hydroxy-2-[[(1R)-2-(4-methoxyphenyl)-1-methylethyl]amino]ethyl]-2(1H)-quinolinone or salt thereof is present in said formulation in an amount of 0.0005% to 0.0016% w/v, based on the total volume of the formulation.

21. The pressurized metered dose inhaler according to claim 12, wherein said co-solvent is present in said formulation in an amount of 6% to 30% by weight, based on the total weight of the formulation.

22. The pressurized metered dose inhaler according to claim 12, wherein said co-solvent is present in said formulation in an amount of 6% to 25% by weight, based on the total weight of the formulation.

23. The pressurized metered dose inhaler according to claim 12, wherein part or all of its internal metallic surfaces are lined with an inert organic coating.

24. The pressurized metered dose inhaler according to claim 23, which is lined with an inert organic coating selected from the group consisting of epoxy-phenol resins, perfluoroalkoxyalkanes, perfluoroalkoxyalkylenes, perfluoroalkylenes, polyether sulfones, copolymers of fluorinated-ethylene-propylene polyether sulfone, and mixtures thereof.

25. A method of filling an aerosol inhaler, said method comprising:
   (a) preparing a solution of one or more active ingredients in one or more co-solvents;
   (b) filling said inhaler with said solution;
   (c) adding a pre-determined amount of phosphoric acid to said solution;
   (d) adding a propellant comprising a hydrofluoroalkane (HFA) to said solution, to obtain a formulation; and
   (e) crimping with valves and gassing, wherein at least one of said active ingredients is 8-hydroxy-5-[(1R)-1-hydroxy-2-[[(1R)-2-(4methoxyphenyl)-1-methylethyl]amino]ethyl]-2(1H)-quinolinone or a salt thereof and is present in an amount of 0.0005% to 0.0032% w/v, based on the total volume of the formulation, and said phosphoric acid is present in an amount equivalent to 0.0004 to 0.040% by weight of 15 M phosphoric acid, based on the total weight of the formulation.

26. The method of claim 25, wherein said 8-hydroxy-5-[(1R)-1-hydroxy-2-[[(1R)-2-(4-methoxyphenyl)-1-methylethyl]amino]ethyl]-2(1H)-quinolinone or a salt thereof is present in an amount of 0.0005% to 0.0016 % w/v, based on the total volume of the formulation.

27. The method of claim 25, wherein said phosphoric acid is present in an amount equivalent to 0.0008 to 0.020% by weight of 15 M phosphoric acid, based on the total weight of the formulation.

28. The method of claim 25, wherein said phosphoric acid is present in an amount equivalent to 0.001 to 0.010% by weight of 15 M phosphoric acid, based on the total weight of the formulation.

29. The formulation according to claim 1, wherein said 8-hydroxy-5-[(1R)-1-hydroxy-2-[[(1R)-2-(4-methoxyphenyl)-1-methylethyl]amino]ethyl]-2(1H)-quinolinone or salt thereof is present in an amount of 0.001% to 0.0016% w/v, based on the total volume of the formulation.

30. The pressurized metered dose inhaler according to claim 12, wherein said 8-hydroxy-5-[(1R)-1-hydroxy-2-[[(1R)-2-(4-methoxyphenyl)-1-methylethyl]amino]ethyl]-2(1H)-quinolinone or salt thereof is present in said formulation in an amount of 0.001% to 0.0016% w/v, based on the total volume of the formulation.

31. The method of claim 25, wherein said 8-hydroxy-5-[(1R)-1-hydroxy-2-[[(1R)-2-(4-methoxyphenyl)-1-methylethyl]amino]ethyl]-2(1H)-quinolinone or a salt thereof is present in an amount of 0.001% to 0.0016% w/v, based on the total volume of the formulation.

* * * * *

UNITED STATES PATENT AND TRADEMARK OFFICE
CERTIFICATE OF CORRECTION

PATENT NO. : 7,381,402 B2  Page 1 of 1
APPLICATION NO. : 11/065569
DATED : June 3, 2008
INVENTOR(S) : Lewis et al.

It is certified that error appears in the above-identified patent and that said Letters Patent is hereby corrected as shown below:

On the title page, Item (30), the Foreign Application Priority Data is missing. Item (30) should read:

-- (30)       Foreign Application Priority Data

May 13, 2004    (EPO) ............................ 04011424 --

Signed and Sealed this

Twelfth Day of August, 2008

JON W. DUDAS
*Director of the United States Patent and Trademark Office*